(12) United States Patent
Lou et al.

(10) Patent No.: US 10,751,267 B2
(45) Date of Patent: Aug. 25, 2020

(54) PERSONAL CARE COMPOSITIONS COMPRISING POORLY SOLUBLE COMPOUNDS

(71) Applicant: Conopco, Inc., Englewood Cliffs, NJ (US)

(72) Inventors: Anjing Lou, Seymour, CT (US); Congling Quan, Woodbridge, CT (US); Maria Buchalova, Sandy Hook, CT (US); Teanoosh Moaddel, Watertown, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 16/470,434

(22) PCT Filed: Dec. 18, 2017

(86) PCT No.: PCT/EP2017/083207
§ 371 (c)(1),
(2) Date: Jun. 17, 2019

(87) PCT Pub. No.: WO2018/114745
PCT Pub. Date: Jun. 28, 2018

(65) Prior Publication Data
US 2019/0328631 A1    Oct. 31, 2019

Related U.S. Application Data

(60) Provisional application No. 62/437,235, filed on Dec. 21, 2016.

(51) Int. Cl.
| | | |
|---|---|---|
| *A61K 8/06* | (2006.01) | |
| *A61K 8/44* | (2006.01) | |
| *A61Q 1/02* | (2006.01) | |
| *A61K 8/36* | (2006.01) | |
| *A61K 8/362* | (2006.01) | |
| *A61K 8/365* | (2006.01) | |
| *A61K 8/49* | (2006.01) | |
| *A61K 8/894* | (2006.01) | |

(52) U.S. Cl.
CPC .............. *A61K 8/064* (2013.01); *A61K 8/068* (2013.01); *A61K 8/361* (2013.01); *A61K 8/362* (2013.01); *A61K 8/365* (2013.01); *A61K 8/442* (2013.01); *A61K 8/447* (2013.01); *A61K 8/498* (2013.01); *A61K 8/894* (2013.01); *A61Q 1/02* (2013.01); *A61K 2800/20* (2013.01); *A61K 2800/805* (2013.01)

(58) Field of Classification Search
None
See application file for complete search history.

(56) References Cited

U.S. PATENT DOCUMENTS

| | | |
|---|---|---|
| 3,274,063 A | 9/1966 | Nieper |
| 3,786,076 A | 1/1974 | Morelle |
| 3,819,825 A | 6/1974 | Goodwin |
| 4,201,235 A | 6/1980 | Ciavatta |
| 4,707,354 A | 11/1987 | Garlen et al. |
| 4,801,579 A * | 1/1989 | Rainer ............... C07K 5/06026 514/5.5 |
| 4,885,157 A | 5/1989 | Fiaschetti |
| 5,133,958 A | 7/1992 | Stuckler |
| 5,198,465 A | 3/1993 | Dioguardi |
| 5,254,331 A | 10/1993 | Mausner |
| 5,416,075 A | 5/1995 | Carson |
| 5,472,706 A | 5/1995 | Friedman |
| 5,582,817 A | 10/1996 | Otsu |
| 5,667,768 A | 9/1997 | Ramin |
| 5,887,747 A | 3/1999 | Burklin et al. |
| 6,013,279 A | 11/2000 | Klett-Loch |
| 6,149,925 A | 11/2000 | Mammone |
| RE37,934 E | 10/2002 | Hoffmann |
| 6,602,492 B2 | 5/2003 | Iwasaki |
| 6,592,908 B1 | 7/2003 | Crum |
| 6,858,217 B2 | 2/2005 | Kerschner |
| 6,869,598 B2 | 3/2005 | Love et al. |
| 6,863,897 B2 | 8/2005 | Love et al. |
| 6,992,062 B2 | 1/2006 | Usala |
| 7,105,570 B2 | 12/2006 | Iwasaki |
| RE39,734 E | 7/2007 | Crum |
| 7,300,649 B2 | 11/2007 | Tanojo |
| 7,740,831 B2 | 6/2010 | Chiba |
| RE42,645 E | 8/2011 | Crum |
| 8,119,111 B2 | 2/2012 | Malek |
| 8,241,681 B2 | 8/2012 | Herrmann |

(Continued)

FOREIGN PATENT DOCUMENTS

| | | |
|---|---|---|
| CA | 2337772 | 1/2000 |
| CN | 101773458 | 7/2010 |

(Continued)

OTHER PUBLICATIONS

Tareen; The Effects of a Glutathione Precursor FT061452 on Serum and Intracellular Glutathione Levels; ClinicalTrials.gov the Effects of a Glutathione Precursor FT061452 on Serum 2013; 2013; .; .; United States of America.
Mela BB Cream Pact IRF 35 SPF 50+/PA+++, Mintel Database GNPD; 2014; XP002778757; pp. 1-5; Korea (South).
Hydrating Mask; Mintel Database GNPD; Aug. 1, 2014; XP002778756; pp. 1-3.
Kumano et al.; Studies of water-in-oil (w/o) emulsion stabilized with amino acids or their salts; Journal Society Cosmetic Chemists; 1977; pp. 285-314; XP001058465; vol. 28, No. 5.
Tareen; The Effects of Short Term Adminstration of a Novel Glutathione Precursor (FTO61452) . . . ; RTRN Research Hub 2012 pp. 1-2; 2012; 1-2.
Search Report and Written Opinion in PCTEP2017083207; dated Mar. 19, 2018.

(Continued)

*Primary Examiner* — Kyung S Chang
(74) *Attorney, Agent, or Firm* — Ellen Plotkin

(57) ABSTRACT

A water-in-oil personal care emulsion with water droplets size below 20 microns, the droplets containing solubilized cystine. A process of making an emulsion is also described.

5 Claims, No Drawings

(56) References Cited

U.S. PATENT DOCUMENTS

| | | | |
|---|---|---|---|
| 8,299,127 | B2 | 10/2012 | Anjing et al. |
| 8,357,649 | B2 | 1/2013 | Chieffi |
| 8,361,446 | B2 | 1/2013 | Muller |
| 8,440,172 | B2 | 5/2013 | Johncock |
| 8,735,442 | B2 | 5/2014 | Ashida et al. |
| 8,795,643 | B1 | 5/2014 | Anthony |
| 8,815,800 | B2 | 8/2014 | Pashkovski |
| 8,865,143 | B2 | 10/2014 | Lu |
| 2003/0194417 | A1 | 10/2003 | Iwasaki |
| 2005/0192229 | A1 | 1/2005 | Perricone |
| 2005/0271726 | A1 | 12/2005 | Crum |
| 2006/0063718 | A1 | 3/2006 | Perricone |
| 2006/0257351 | A1 | 11/2006 | Chiba |
| 2009/0263513 | A1 | 10/2009 | Marini |
| 2010/0305169 | A1 | 12/2010 | Robinson |
| 2010/0322876 | A1 | 12/2010 | Nguyen |
| 2011/0183040 | A1 | 7/2011 | Ermolin |
| 2012/0034183 | A1 | 2/2012 | Cohen |
| 2014/0162979 | A1 | 6/2014 | Palla-Venkata |
| 2016/0120782 | A1 | 5/2016 | Lee |
| 2017/0079895 | A1 | 3/2017 | Edelson et al. |
| 2017/0112764 | A1 | 4/2017 | Wu |

FOREIGN PATENT DOCUMENTS

| | | |
|---|---|---|
| CN | 101797213 | 11/2010 |
| CN | 102150866 | 8/2011 |
| CN | 102366397 | 3/2012 |
| CN | 105919827 | 7/2016 |
| CN | 107411982 | 12/2017 |
| EP | 0815040 | 10/1996 |
| EP | 1269978 | 1/2003 |
| EP | 2572701 | 3/2013 |
| EP | 2921160 | 9/2015 |
| FR | 2608424 | 6/1988 |
| FR | 2660196 | 10/1991 |
| FR | 2997852 | 5/2014 |
| GB | 720561 | 12/1954 |
| GB | 874368 | 8/1961 |
| GB | 987800 | 3/1965 |
| GB | 1050756 | 12/1966 |
| GB | 2212722 | 8/1989 |
| JP | 61227515 | 10/1986 |
| JP | 5032533 | 2/1993 |
| JP | 2009242321 | 10/2009 |
| JP | 2010280675 | 12/2010 |
| JP | 2014196275 | 10/2014 |
| JP | 2015030689 | 2/2015 |
| JP | 2006001903 | 1/2016 |
| KR | 20160123753 | 10/2016 |
| WO | WO9505852 | 3/1995 |
| WO | WO9913819 | 3/1999 |
| WO | WO0003689 | 1/2000 |
| WO | WO0025740 | 5/2000 |
| WO | WO0069403 | 11/2000 |
| WO | WO03080011 | 10/2003 |
| WO | WO03105806 | 12/2003 |
| WO | WO04082654 | 9/2004 |
| WO | WO2004103353 | 12/2004 |
| WO | WO2005097060 | 10/2005 |
| WO | WO2007021065 | 2/2007 |
| WO | WO2007070069 | 6/2007 |
| WO | WO2010090546 | 8/2010 |
| WO | WO2010113925 | 10/2010 |
| WO | WO2011155280 | 12/2011 |
| WO | WO2012002669 | 1/2012 |
| WO | WO2012094638 | 7/2012 |
| WO | WO2013044111 | 3/2013 |
| WO | WO1309250 | 6/2013 |
| WO | WO2015005563 | 1/2015 |
| WO | WO2016033183 | 3/2016 |
| WO | 105919827 | 9/2016 |

OTHER PUBLICATIONS

L-Cystine; Sigma-Aldrich Product Information C8755.
Meister; Selective Modification of Glutathione Metabolism; Science 200 vol. 220 1985 pp. 471-477; 1985; pp. 471-477; 220.
Meister, Alton; Glutathione Metabolism and Its Selective Modification; J Biol Chem; Nov. 25, 1988; pp. 17205-17208; vol. 263, No. 33.
IPRP2 in PCTCN2017117008; Apr. 22, 2019.
Search Report and Written Opinion in PCTCN2017117008; dated Mar. 27, 2018.
Constantinides et al.; Enhanced intestinal absorption of an RGD peptide from water-in-oil microemulsions of different composition and particle size; Journal of Controlled Release; 1995; 109-116; vol. 34.
Search Report and Written Opinion in EP18173916; dated Oct. 23, 2018; European Patent Office (EPO).
Search Report in EP17156112; dated Apr. 7, 2017.
Dolphin; Glutathione: Chemical, biochemical and medical aspects; Cell Biochemistry & Function Apr. 1990 vol. 8 Issue 2 pp. 139; Apr. 1990; 139; vol. 8, Iss 2; United States of America.
Meister; Glutathione Metabolism and Its Selective Modification; The Journal of Biological Chemistry ; 1988; pp. 17205-17208; vol. 263 No. 33; United States of America.
Tyrrell; Correlation Between Endogenous Glutathione Content and Sensitivity of CulturedHuman Skin Cells . . . ; Photochemistry and Photobiology 1988 vol. 47 No. 3 pp. 405-412; 1988; p. 405-412; vol. 47, No. 3; United States of America.
Search Report and Written Opinion in EP16169468; dated Oct. 14, 2016.
Search Report & Written Opinion in EP17156128; dated Apr. 7, 2017.
Search Report and Written Opinion in PCTEP2017083223; dated Mar. 23, 2018.
Molding Cream; Mintel GNPD; 2005; pp. 1-2; XP002778899.
Ja Yoon Cream; Mintel GNPD; 2016; pp. 1-6; XP002778901.
Frizz and Stray Hair Control Cream; Mintel GNPD; 2006; pp. 1-2; XP002778900.
Written Opinion in PCTEP2017083207.
Written Opinion 2 in PCTEP2017083223; dated Jan. 15, 2019.
Anonymous; Conditioner; Mintel GNPD Conditioner; Mar. 22, 2007; pp. 1-2; XP055522806.
Anonymous; Shape & Life Volumising Gel; Mintel GNPD Shape & Lift Volumising Gel; Apr. 11, 2007; pp. 1-2; XP055522803.
IPRP in PCTEP2017083207; dated Mar. 1, 2019.
Search Report and Written Opinion in PCTCN2017117015; dated Mar. 23, 2018.
IPRP in PCTEP2017083223; Apr. 3, 2019.
Search Report and Written Opinion in PCTCN2017117006; dated Mar. 14, 2018.
Search Report and Written Opinion in PCTCN2017116999; dated Mar. 20, 2018.
IPRP2 in PCTCN2017117006; Apr. 25, 2019.
IPRP2 in PCTCN2017116999; Apr. 26, 2019.
IPRP2 in PCTCN2017117015; Apr. 26, 2019.
Supplementary Search Report and Written Opinion in EP17883107; dated Dec. 11, 2019.
Search Report and Written Opinion in EP17882397; dated Aug. 27, 2019.
Supplemental Search Report and Written Opinion in EP17885031; dated Nov. 11, 2019.
Mintel GNPD; Hydra-Filler Pro-Youth Boosting Moisturizer; 2013; pp. 1-3 (Record ID 2117408).
Mintel GNPD; Hyal-Defence Hyaluronic Acid Protection Serum; 2012; pp. 1-3 (Record ID 1850085).
Co-Pending Application, Guelakis, et al, filed Jun. 17, 2019, U.S. Appl. No. 16/470,425.
Co-Pending Application, Damodaran, et al, filed Jun. 17, 2019, U.S. Appl. No. 16/470,391.
Co-Pending Application, Damodaran, et al, filed Jun. 17, 2019, U.S. Appl. No. 16/470,426.
Co-Pending Application, Guelakis, et al, filed Jun. 17, 2019, U.S. Appl. No. 16/470,439.

(56) References Cited

OTHER PUBLICATIONS

Co-Pending Application, Buchalova, et al, filed Jun. 17, 2019, U.S. Appl. No. 16/470,513.

* cited by examiner

PERSONAL CARE COMPOSITIONS COMPRISING POORLY SOLUBLE COMPOUNDS

FIELD OF THE INVENTION

The invention relates to topical personal care compositions containing ingredients which are minimally soluble within the pH range suitable for application to skin.

BACKGROUND OF THE INVENTION

Topical personal care compositions must be formulated at a skin-tolerant pH range, but many of the cosmetically beneficial compounds have very low solubility at that pH, their solubility being substantially higher at a very alkaline or very acidic pH, outside of the pH range tolerated by skin. Some examples of such compounds are salicylic acid, fumaric acid, azelaic acid, sorbic acid, uric acid, alginic acid, amino acids and other zwitterionic compounds such as for example tyrosine, isoleucine, tryptophan, phenylalanine. One of such compounds, for example, is cystine. This is unfortunate because cystine can serve as a building block for glutathione production in the body. Glutathione (GSH) is a tripeptide that consists of glutamate, cysteine, and glycine. It is present in all mammalian tissues. It is the main anti-oxidant in the living body: it protects cells from oxidation by quenching reactive oxygen species. GSH is believed to play a significant role in protecting cells against the cytotoxic effects of ionizing radiation, heat, certain chemicals, and significantly, solar UV radiation (Tyrell et al., Photochem. Photobiol. 47: 405-412, 1988; Meister, J. Biol. Chem. 263: 205-217, 1988; Meister, Science 200:471-477, 1985). While true in all areas of the body, this is particularly important in the skin, which is so greatly exposed to the damaging effects of radiation, particularly UV radiation, and environmental pollutants. Decrease in the intracellular concentration of glutathione in skin is associated with cell damage, inflammation, skin darkening, discoloration, spots or freckles caused by exposure to ultraviolet radiation, physiological aging, and the like. It is, therefore, highly desirable to enhance the generation of glutathione in skin.

A logical approach would seem to be to provide cells with an exogenous source of GSH (e.g. through ingestion or topical delivery). Unfortunately, GSH is not bioavailable when administered exogenously, i.e. where localized extracellularly, it is broken down into its constituent amino acids (glutamate, cysteine, and glycine) for cellular uptake and synthesis of the GSH tripeptide. Thus, GSH is not directly transported into the cells and therefore does not itself result in an intracellular increase of glutathione. Biosynthesis of GSH occurs in the cell in a tightly regulated manner. The quantity of glutathione in cells depends to a large degree on the availability of cysteine in the cells. Cysteine, a composite amino acid of GSH, may increase cellular levels of GSH, but exposed sulfhydryl group of cysteine renders it unstable and reactive and also causes strong unpleasant odor. Unlike cysteine, cystine can be administered safely; cystine is transported into the cell and converted to cysteine within the cell, the cysteine then being available for intracellular GSH production.

Topical compositions containing various amino acids and other skin care actives have been described, see e.g. Tanojo U.S. Pat. No. 7,300,649B2, Laboratoire Filorga product, Schlachter WO 00/03689, Ermolin et al. US2011183040, Garlen et al. U.S. Pat. No. 4,707,354, Muller et al. U.S. Pat. No. 8,361,446, Hermann et al. U.S. Pat. No. 8,241,681. Compositions for potentiating intracellular glutathione production have been described. See e.g. Chiba et al. U.S. Pat. No. 7,740,831, Crum et al (USRE37934, USRE42645, WO2016/033183, and US20050271726); Mammone U.S. Pat. No. 6,149,925, and Perricone US 20060063718.

Cystine is normally derived from the diet. Delivery of cystine from topical compositions, however, is challenging due to its extremely low solubility in biologically acceptable vehicle at a skin-tolerant pH range. The solubility of cystine in water is 0.112 mg/ml at 25° C.; cystine is more soluble in aqueous solutions with pH less than 2 or pH above 8. Efforts have been made to increase L-Cystine solubility. See e.g. Erich Königsberger, Zhonghua Wang, Lan-Chi Königsberger Solubility of L-Cystine in NaCl and Artificial Urine Solution; *Monatshefte für Chemie*, January 2000, Volume 131, Issue 1, pp 39-45; Hsieng-Cheng TsengHsieng-Cheng Tseng et. al, Solubilities of amino acids in water at various pH values under 298.15 K, Fluid Phase Equilibria 285(1): 90-95•October 2009; F. Apruzzese, et. al Protonation equilibria and solubility of L-Cystine, Talanta, 56, 459-469, 2002; C. Bretti, et. al Solubility and activity coefficients of acidic and basic noneelectrolytes in aqueous salt solutions. J. Chem. Eng. Data, 50, 1761-1767, 2005; Michael D. Ward, Jeffrey D. Rimer, U.S. Pat. No. 8,450,089; Michael D. Ward, Zina Zhou, U.S. Pat. No. 8,916,609; Hara, et. al U.S. Pat. No. 5,316,767; Longqin Hu, US 2014/0187546.

The present invention is based in part on a surprising finding that compounds, such as cystine, may be solubilized in topical personal care compositions at a skin tolerant pH range, at substantially the same level as cystine's solubility at high or low pH.

SUMMARY OF THE INVENTION

In one embodiment, the invention includes a process of making a topical water-in-oil personal care emulsion composition, the process comprising the steps of:
 a. mixing from about 0.5 to about 10% of cystine in basic aqueous solution at pH of from 9 to 14, to obtain an aqueous solution of cystine;
 b. mixing the aqueous solution of cystine with a cosmetically acceptable oil and with from 1 to 15% of an emulsifier with HLB from 1 to 12, to obtain a water-in-oil pre-emulsion;
 c. mixing the pre-emulsion with an aqueous acidic solution at pH of from 1 to 4.5; and
 d. reducing the pH of the pre-emulsion to the pH range of from 3.5 to 8.5 and reducing the droplet size of the aqueous phase in the pre-emulsion such that from 90% to 100% of the droplets have a diameter in the range of from 100 nm to 20 microns,
 wherein the emulsion comprises from 10 to 70% of aqueous phase, with the weight ratio of the basic aqueous solution to the acidic aqueous solution is in the range of from 4:1 to 1:1.

DETAILED DESCRIPTION OF THE INVENTION

Throughout the specification and claims, the following terms take the meanings explicitly associated herein, unless the context clearly dictates otherwise.

The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention. In addition, each of the examples given in connection with the various embodiments of the invention which are intended to be illustrative, and not restrictive.

Except in the examples, or where otherwise explicitly indicated, all numbers in this description indicating amounts of material or conditions of reaction, physical properties of materials and/or use are to be understood as modified by the word "about." All amounts are by weight of the final composition, unless otherwise specified. The disclosure of the invention as found herein is to be considered to cover all embodiments as found in the claims as being multiply dependent upon each other irrespective of the fact that claims may be found without multiple dependency or redundancy. In specifying any range of concentration or amount, any particular upper concentration can be associated with any particular lower concentration or amount.

"Comprising" is intended to mean "including" but not necessarily "consisting of" or "composed of." In other words, the listed steps or options need not be exhaustive.

"Skin" is meant to include skin on the face, neck, chest, back, arms (including underarms), hands, legs, buttocks and scalp.

"Leave-on composition" refers to a composition that is applied to the skin and is not intended to be washed or rinsed off for some period of time, specifically hours, as contrasted with skin cleansing or wash-off or rinse-off compositions which are rinsed off or washed off immediately or minutes after the application.

"Non-solid" with respect to the composition means that the composition has a measurable viscosity (measurable for instance with a Brookfield Viscometer DV-I+(20 RPM, RV6, 30 Seconds, 20° C.) in the range of from 1 Pas to 500 Pas, preferably from 2 Pas to 100 Pas, more preferably from 3 Pas to 50 Pas.

"Personal care composition" refers to any product applied to a human body for improving appearance, sun protection, cleansing, odor control, moisturization or general aesthetics. Non-limiting examples of personal care compositions include skin lotions, creams, gels, lotions, sticks, shampoos, conditioners, shower gels, toilet bars, antiperspirants, deodorants, shave creams, depilatories, lipsticks, foundations, mascara, sunless tanners and sunscreen lotions.

"Skin cosmetic composition" refers to any product applied to a human body for improving appearance, sun protection, reducing wrinkled appearance or other signs of photoaging, odor control, skin lightening, even skin tone, or general aesthetics. Non-limiting examples of topical cosmetic skin compositions include skin lotions, creams, gels, sticks, antiperspirants, deodorants, lipsticks, foundations, mascara, liquid or gel body washes, soap bars, sunless tanners and sunscreen lotions.

Personal care composition prepared by the present technology is preferably a leave-on non-solid skin cosmetic composition, because such compositions are the most challenging in terms of incorporating cystine due to its low solubility. Increased solubility of cystine in the compositions increases availability of cystine for greater delivery through skin and improved skin feel of the composition (reduces grittiness).

In one embodiment, the compositions of the invention are made by the process according to the invention.

In one embodiment, the process according to the invention includes the steps of:

Step a.: mixing from 0.5 to 10%, or 0.5 to 1.3%, of cystine in basic aqueous solution at pH of from 9 to 14, or 9 to 12, or 9 to 10, or 9.4, to obtain an aqueous solution of cystine. The basic aqueous solution is prepared with a suitable strong base, including but not limited to alkali and alkaline metal hydroxides, monoethanol amine, diethanol amine, triethanol amine, and mixtures thereof. The higher the amount of cystine the higher the pH of the basic solution is required. The solution is prepared at room temperature using a gentle agitation until no visible crystals are seen.

Step b.: mixing the aqueous solution of cystine with a cosmetically acceptable oil and with from 1 to 15% of an emulsifier with HLB from 1 to 12, or from 1 to 10, or from 1 to 9, to obtain a water-in-oil pre-emulsion.

The emulsification process is conducted at the temperature that is not higher than 60° C. and preferably at room temperature using any low shear device.

Step c.: mixing the pre-emulsion with an aqueous acidic solution at pH of from 1 to 4.5, or from 1 to 4, or from 1 to 3.5. The acidic aqueous solution is prepared with any suitable strong acid, including but not limited to: mineral acids (hydrochloric, sulfuric, nitric, phosphoric, bromic), fatty acids, ascorbic, glycolic, lactic, other hydroxycarboxylic acids, and di- and polycarboxylic acids.

Step d.: Pre-emulsion is passed through a high shear device to achieve a target pH range from 3.5-8.5 and reduce aqueous drop size such that substantially all droplets, or at least 90%, or at least 95% of the droplets, or at least 98%, or 99% of the droplets have a diameter in the range of from 100 nm to 20 microns, or in the alternative from 200 nm to 15 microns, or from 300 nm to 12 microns, or from 400 nm to 10 microns. When the drop size of the emulsion is smaller than 20 microns cystine recrystallization is prevented, even though the emulsion is at neutral pH.

In one embodiment, the water droplet size is reduced by subjecting the pre-emulsion to high shear. In one embodiment, the water droplet size is reduced by homogenizing the pre-emulsion. In one embodiment, the water droplet size is reduced by sonolating the pre-emulsion. Suitable equipment includes but is not limited to Nano DeBee homogenizer of BEE International (Massachusetts, USA) and sonolator homogenizer manufactured by Sonic Corporation of Connecticut, USA. This process is completed at room temperature. The Nano DeBee is operated at pressures of between $3.45 \times 10^6$ and $1.38 \times 10^7$ Pas the rotor/Stator types of high shear devices operate with rotor speeds between 2000 and 6000 rpm.

Size of the droplets in the emulsion is determined by optical and/or electron microscopy and image analysis. For example, the emulsion photomicrographs can be evaluated visually or can be digitized and the number of different-sized particles measured with image analysis software.

It is important to both employ a sufficient amount of acidic solution and mixing energy to ensure thorough mixing and coalescence of the acidic solution with the water droplets in the pre-emulsion obtained in step b. Sequential emulsification of the high pH solution (cystine solution) and adding low pH solutions in the process ensures that cystine stays in high pH environment so that it is fully solubilized before step d. Final pH reduction to target pH occurs during step d.

In the inventive process, cystine does not recrystallize. Alternatively if cystine is simply admixed with the neutral pH composition, the cystine agglomerates forming millimeter sized crystals and results in an undesirable grainy texture leading to undesirable sensory performance of the product.

In addition, since cystine is not solubilized, it is inhomogeneously dispersed throughout the formulation and thereby impacts bioavailability.

Together, the basic and the acidic aqueous solutions in steps (a) and (c) form an aqueous phase of the final water-in-oil emulsion. The emulsion comprises from 10 to 70%, or from 15 to 60%, or from 20 to 50% aqueous phase by weight of the emulsion. The weight ratio of the basic aqueous solution to the acidic aqueous solution is in the range of from 4:1 to 1:1, or in the alternative from 3:1 to 1:1, or in the alternative 2:1. Typically the higher volume of the aqueous phase will result in increasing size of water droplets and increase in viscosity of the emulsion.

In one embodiment, the pH of the personal care composition is between 3.5 and 8.5. In some embodiments, the pH of the personal care composition is between pH 3.5 and pH 8. In some embodiments, the pH of the personal care composition is between pH 5 to pH 7.8. In some embodiments, the pH of the personal care composition is between 5 and 7.5.

Suitable oils include emollients, fatty acids, fatty alcohols, thickeners and combinations thereof. These may be in the form of silicone oils, natural or synthetic esters, hydrocarbons, alcohols and fatty acids. Amounts of the emollients may range anywhere from 0.1 to 95%, preferably between 1 and 50% by weight of the composition.

Silicone oils may be divided into the volatile and non-volatile variety. The term "volatile" as used herein refers to those materials which have a measurable vapor pressure at ambient temperature. Volatile silicone oils are preferably chosen from cyclic (cyclomethicone) or linear polydimethylsiloxanes containing from 3 to 9, preferably from 5 to 6, silicon atoms.

Nonvolatile silicone oils useful as an emollient material include polyalkyl siloxanes, polyalkylaryl siloxanes and polyether siloxane copolymers. The essentially nonvolatile polyalkyl siloxanes useful herein include, for example, polydimethyl siloxanes with viscosities of from $5 \times 10^{-6}$ to 0.1 m$^2$/s at 25° C. Among the preferred nonvolatile emollients useful in the present compositions are the polydimethyl siloxanes having viscosities from $1 \times 10^{-5}$ to about $4 \times 10^{-4}$ m$^2$/s at 25° C.

Another class of nonvolatile silicones are emulsifying and non-emulsifying silicone elastomers. Representative of this category is Dimethicone/Vinyl Dimethicone Crosspolymer available as Dow Corning 9040, General Electric SFE 839, and Shin-Etsu KSG-18. Silicone waxes such as Silwax WS-L (Dimethicone Copolyol Laurate) may also be useful.

Among the ester emollients are:

a) Alkyl esters of saturated fatty acids having 10 to 24 carbon atoms. Examples thereof include behenyl neopentanoate, isononyl isonanonoate, isopropyl myristate and octyl stearate.

b) Ether-esters such as fatty acid esters of ethoxylated saturated fatty alcohols.

c) Polyhydric alcohol esters. Ethylene glycol mono- and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. Particularly useful are pentaerythritol, trimethylolpropane and neopentyl glycol esters of 01-030 alcohols.

d) Wax esters such as beeswax, spermaceti wax and tribehenin wax.

e) Sugar ester of fatty acids such as sucrose polybehenate and sucrose polycottonseedate.

Natural ester emollients principally are based upon mono-, di- and tri-glycerides. Representative glycerides include sunflower seed oil, cottonseed oil, borage oil, borage seed oil, primrose oil, castor and hydrogenated castor oils, rice bran oil, soybean oil, olive oil, safflower oil, shea butter, jojoba oil and combinations thereof. Animal derived emollients are represented by lanolin oil and lanolin derivatives. Amounts of the natural esters may range from 0.1 to 20% by weight of the compositions.

Hydrocarbons which are suitable cosmetically acceptable carriers include petrolatum, mineral oil, $C_{11}$-$C_{13}$ isoparaffins, polybutenes and especially isohexadecane, available commercially as Permethyl 101A from Presperse Inc.

Fatty acids having from 10 to 30 carbon atoms may also be suitable as cosmetically acceptable carriers. Illustrative of this category are pelargonic, lauric, myristic, palmitic, stearic, isostearic, oleic, linoleic, linolenic, hydroxystearic and behenic acids and mixtures thereof.

Fatty alcohols having from 10 to 30 carbon atoms are another useful category of cosmetically acceptable carrier. Illustrative of this category are stearyl alcohol, lauryl alcohol, myristyl alcohol, oleyl alcohol and cetyl alcohol and mixtures thereof.

Preferred are emollients that can be used, especially for products intended to be applied to the face, to improve sensory properties and are chosen from the group of polypropylene glycol-14 butyl ether otherwise known as Tegosoft PBE, or PPG15 stearyl ether such as Tegosoft E, other oils such as esters, specifically, isopropyl myristate, isopropyl palmitate, other oils could include castor oils and derivatives thereof.

Emulsifier is included in an amount of from 1 to 15%, or from 1 to 12% or from 1 to 10%.

The type and the amount of the emulsifier is chosen depending on emulsion composition and the need to ensure stability of small aqueous drops. In one embodiment, the emulsifier is selected from the group consisting of ethoxylated nonionic surfactants; polyglycerol esters, sucrose poly fatty ester, silicone emulsifiers, e.g. PEG 10 dimethicone, or Lauryl PEG-10 Tris(trimethylsiloxy)silylethyl Dimethicone (ES5300 from Dow Corning). In an alternative embodiment, non-limiting examples of some suitable emulsifiers include SIMALINE WO (PEG-30 Dipolyhydroxystearate; available from Seppic), FLUID ANOV 20X (Octyl dodecanol & Octyldodecyl Xyloside; available from Seppic), ES-5300 (Lauryl PEG-10 Tris(trimethylsiloxy)silylethyl Dimethicone; from Dow Corning), Abil EM90 (Cetyl PEG/PPG-10/1 Dimethicone; available from Evonik) and Abil WE09 (Polyglyceryl-4 Isostearate and Cetyl PEG/PPG-10/1 Dimethicone and Hexyl Laurate; available from Evonik). Yet other illustrative examples include those generally classified as polyether modified silicone surfactants like PEG/PPG-20/22 butyl ether dimethicone, PEG-3 dimethicone, PEG-9 methyl ether dimethicone, PEG-10 dimethicone, mixtures thereof or the like. The emulsifiers are made available from suppliers like Shin-Etsu and sold under the names KF-6015, KF-6016, and KF-6017, respectively. Another emulsifier suitable for use is DC5225C (Cyclopentasiloxane (and) PEG/PPG-18/18 Dimethicone0 from Dow Corning. In one embodiment the emulsifier is ES5300, KF-6017 (PEG-10 dimethicone), DC5225C, ES-5300 or a mixture thereof.

All additional ingredients as described below can be incorporated into the composition at any point during the emulsification process.

The emulsion compositions of the present invention preferably include additional ingredients to enhance the ability of cystine to enable intracellular GSH synthesis. In one embodiment, the emulsion comprises additional amino acids, especially either glycine or glutamate or both. Amino acids included in the inventive composition are present as L stereo isomers, since this is the most abundant and natural isomeric form found in nature. Since the building blocks of naturally-occurring proteins found in human skin, hair and nails are amino acids with the L isomeric form, it is expected that L stereo isomer amino acids contained within personal care products of the present invention can have a greater interaction with these proteins that is intrinsically more biocompatible in nature compared to the D stereo isomeric form. In addition, commercial production and supply of L stereo isomer amino acids is significantly higher compared to the D stereo isomeric form. Finally, L stereo isomer amino acids are also more cost effective to produce, more sustainable, more eco-friendly and available at a lower cost compared to D stereo isomer amino acids.

Any of the amino acids included in the present invention may be in the form of a salt, and the term "cystine," "glutamate source", and "glycine" used in the present specification also encompasses salts. Such salt is not particularly limited as long as it is acceptable for topical application. For example, salts with inorganic acid or organic acid can be mentioned. As the inorganic acid, for example, hydrochloric acid, hydrobromic acid, nitric acid, sulfuric acid, phosphoric acid and the like can be mentioned, and as the organic acid, formic acid, acetic acid, trifluoroacetic acid, propionic acid, lactic acid, tartaric acid, oxalic acid, fumaric acid, maleic acid, citric acid, malonic acid, methanesulfonic acid and the like can be mentioned. As the salt with a base, for example, alkali metal salts such as sodium salt, potassium salt and the like, alkaline earth metal salts such as calcium salt, magnesium salt and the like, and the like can be mentioned.

Glutamate source can be present in the form of its functional equivalents—glutamine, glutamic acid and/or pyroglutamic acid and/or their salts may be employed. Pyroglutamic acid (and/or salts thereof) is preferred since it is more stable than glutamine or glutamic acid. In one embodiment, amino acids in GSH precursor are cystine and pyroglutamic acid (and/or salts thereof). In one embodiment, amino acids in GSH precursor are cystine and pyroglutamic acid and glycine (and/or salts thereof).

In one embodiment, the composition of the invention is a leave-on non-solid composition in the form of a personal care topical emulsion, lotion, gel, cream, or vanishing cream comprising glutathione precursor which comprises cystine, glutamate (especially pyroglutamic acid or salt thereof, e.g. sodium pyroglutamate) and glycine, at pH of 3.5 to 8.5, especially at pH of 5 to 8.

In one embodiment, the composition of the invention is a leave-on non-solid composition in the form of a personal care topical emulsion, lotion, gel, cream, or vanishing cream comprising glutathione precursor which comprises cystine, glutamate, and glycine at pH of 3.5 to 8.5, especially at pH of 5 to 8.

In one embodiment, glutamate source (preferably pyroglutamate) is included in an amount of from 0.01 to 10%, or in the alternative of from 0.01 to 5%, or from 0.05 to 1%, or in the alternative from 0.05 to 0.5%. In one embodiment, glycine source is included in an amount of from 0.01 to 10%, or in the alternative of from to 0.01 to 5%, or from 0.05 to 1%, or in the alternative from 0.05 to 0.5%.

Thickeners or rheology modifiers can be utilized as part of the present invention. Typical thickeners include crosslinked acrylates (e.g. Carbopol 982®), hydrophobically-modified acrylates (e.g. Carbopol 1382®), polyacrylamides (e.g. Sepigel 305®), acryloylmethylpropane sulfonic acid/salt polymers and copolymers (e.g. Aristoflex HMB® and AVC®), cellulosic derivatives and natural gums. Among useful cellulosic derivatives are sodium carboxymethylcellulose, hydroxypropyl methocellulose, hydroxypropyl cellulose, hydroxyethyl cellulose, ethyl cellulose and hydroxymethyl cellulose. Natural gums suitable for the present invention include guar, xanthan, *sclerotium*, carrageenan, pectin and combinations of these gums. Inorganics may also be utilized as thickeners, particularly clays such as bentonites and hectorites, fumed silicas, talc, calcium carbonate and silicates such as magnesium aluminum silicate (Veegum®). Amounts of the thickener may range from 0.0001 to 10%, usually from 0.001 to 1%, or from 0.01 to 0.5%.

Humectants of the polyhydric alcohol-type can be included. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. The amount of humectant may range anywhere from 0.5 to 50%, preferably between 1 and 15% by weight of the composition.

Skin moisturizers, e.g. hyaluronic acid and/or its precursor N-acetyl glucosamine may be included. N-acetyl glucosamine may be found in shark cartilage or shitake mushrooms and are available commercially from Maypro Industries, Inc (New York). Other preferred moisturizing agents include hydroxypropyl tri($C_1$-$C_3$ alkyl)ammonium salts. These salts may be obtained in a variety of synthetic procedures, most particularly by hydrolysis of chlorohydroxypropyl tri($C_1$-$C_3$ alkyl)ammonium salts. A most preferred species is 1,2-dihydroxypropyltrimonium chloride, wherein the $C_1$-$C_3$ alkyl is a methyl group. Amounts of the salt may range from 0.2 to 30%, and preferably from 0.5 to 20%, optimally from 1% to 12% by weight of the topical composition, including all ranges subsumed therein.

Ordinarily the $C_1$-$C_3$ alkyl constituent on the quaternized ammonium group will be methyl, ethyl, n-propyl, isopropyl or hydroxyethyl and mixtures thereof. Particularly preferred is a trimethyl ammonium group known through INCI nomenclature as a "trimonium" group. Any anion can be used in the quat salt. The anion may be organic or inorganic with proviso that the material is cosmetically acceptable. Typical inorganic anions are halides, sulfates, phosphates, nitrates and borates. Most preferred are the halides, especially chloride. Organic anionic counter ions include methosulfate, toluoyl sulfate, acetate, citrate, tartrate, lactate, gluconate, and benzenesulfonate.

Still other preferred moisturizing agents which may be used, especially in conjunction with the aforementioned ammonium salts include substituted urea like hydroxymethyl urea, hydroxyethyl urea, hydroxypropyl urea; bis(hydroxymethyl) urea; bis(hydroxyethyl) urea; bis(hydroxypropyl) urea; N,N'-dihydroxymethyl urea; N,N'-dihydroxyethyl urea; N,N'-di-hydroxypropyl urea; N,N,N'-trihydroxyethyl urea; tetra(hydroxymethyl) urea; tetra (hydroxyethyl) urea; tetra(hydroxypropyl urea; N-methyl, N'-hydroxyethyl urea; N-ethyl-N'-hydroxyethyl urea; N-hydroxypropyl-N'-hydroxyethyl urea and N,N'dimethyl-N-hydroxyethyl urea. Where the term hydroxypropyl appears, the meaning is generic for either 3-hydroxy-n-propyl, 2-hydroxy-n-propyl, 3-hydroxy-i-propyl or 2-hydroxy-i-propyl radicals. Most preferred is hydroxyethyl urea. The latter is available as a 50% aqueous liquid from the National Starch & Chemical Division of ICI under the trademark Hydrovance.

Amounts of substituted urea that may be used in the topical composition of this invention range from 0.01 to 20%, or from 0.5 to 15%, or from 2 to 10%.

When ammonium salt and substituted urea are used, in a most especially preferred embodiment at least from 0.01 to 25%, or from 0.2 to 20%, or from 1 to 15% humectant, like glycerine, is used. Further moisturizing agents for use herein include petrolatum and/or various aquaporin manipulating actives and/or oat kernel flour.

In some embodiments, the personal care composition, and especially a leave-on skin cosmetic composition of the present invention contains sun-screen. These are typically a combination of organic and inorganic sunscreens. It is particularly important to include both UV-A and UV-B radiation sunscreens.

UV-B sunscreen oil may be selected from the class of cinnamic acid, salicylic acid, diphenyl acrylic acid, or derivatives thereof. The UV-B sunscreen oil may include one or more of octyl salicylate, 3,3,5-trimethylcyclohexyl 2-hydroxybenzoate, ethylhexyl salicylate, 2-ethylhexyl 2-cyano-3,3-diphenyl-2-propenoate, or 2-ethylhexyl-4-methoxycinnamate (also known as octyl methoxycinnamate or "OMC"). Such UV-B sunscreen oils are typically commercially available, such as Octisalate™ (octyl salicylate), Homosalate™ (3,3,5-trimethyleyclohexyl 2-hydroxybenzoate), NeoHeliopan™ (a range of organic UV filters including OMC (Neo Heliopan AV™) and ethylhexyl salicylate (Neo Heliopan OS™)), Octocrylene™ and Milestab 3039™ (2-ethylhexyl-2-cyano-3,3-diphenyl-2-propenoate) or Parsol MCX™ (2-ethylhexyl-4-methoxycinnamate). The amount of UV-B sunscreen oil in the personal care composition may be 0.1 wt % to 20 wt %, or 0.2 wt % to 10 wt %, or 0.5 wt % to 7 wt %, or 2 wt % to 6 wt %.

The personal care composition may further include a UV-B sunscreen that is water-soluble. The water soluble UV-B sunscreen may also include phenylbezimidazole sulfonic acid (also known as ensulizole), 4-aminobenzoic acid (also known as para-aminobenzoic acid or "PABA"), or both.

The personal care composition of any one of the above embodiments may further include 0.1 wt % to 10 wt % of a UV-A sunscreen oil. The UV-A sunscreen oil may include one or more of 4-t-butyl-4'-methoxydibenzoylmethane ("avobenzone"), 2-methyldibenzoylmethane, 4-methyldibenzoyl-ethane, 4-isopropyldibenzoyl-methane, 4-tert-butyldibenzoylmethane, 2,4-dimethyldibenzoylmethane, 2,5-dimethyldibenzoylmethane, 4,4'-diisopropyldibenzoylmethane, 2-methyl-5-isopropyl-4'-methoxy-dibenzoylmethane, 2-methyl-5-tert-butyl-4'-methoxy-dibenzoylmethane, 2,4-dimethyl-4'-methoxydibenzoylmethane, 2,6-dimehyl-4-tert-butyl-4'methoxy-dibenzoylmethane, diethylaminohydroxybenzoyl hexyl benzoate, ecamsule, or methyl anthranilate. The amount of UV-A sunscreen oil in the personal care composition may be 0.5 wt % to 7 wt %, or 1 wt % to 5 wt %.

Additional suitable sunscreen oils suitable for use in the personal care composition include those commercially available from BASF corporation: Uvinul T-150 (Ethylhexyl triazone; a UV-B sunscreen oil), Uvinul A Plus (Diethylamino hydroxybenzoyl hexyl benzoate; a UV-A sunscreen oil), Tinosorb S (bis-ethylhexyloxyphenol methoxyphenyl triazine; a UV-A and UV-B sunscreen oil), Tinosorb M(methylene bisbenzotriazolyl tetramethylbutylphenol; a UV-A and UV-B sunscreen oil). Bisdisulizone disodium may also be included in the personal care composition.

A particularly preferred combination of UV-A and UV-B sunscreen oils is avobenzone and 2-ethylhexyl-4-methoxycinnamate.

In some embodiments, the sunscreen is an inorganic sunscreen. Examples of inorganic sunscreens suitable for use in the skin care composition of the present invention include, but are not limited to, microfine titanium dioxide, zinc oxide, polyethylene and various other polymers. By the term "microfine" is meant particles of average size ranging from 10 to 200 nm, alternatively from 20 to 100 nm. Amounts of the sunscreen when present in a skin care formulation according to some embodiments of the present invention may range from 0.1% to 30%, alternatively from 2% to 20%, alternatively from 4% to 10% by weight of the composition.

It has been taught that selenium source, e.g. selenomethionine, is an essential ingredient, along with constituent amino acids of GSH, for enabling GSH intracellular biosynthesis. It has been found as part of the present invention, however, that a selenium source is not necessary, and is indeed superfluous, to achieve intracellular increase in GSH content according to the present invention. Although selenium source may be included, it is preferably avoided in topical skin care compositions of the invention because it is considered a skin sensitizer under some regulatory regimes. Accordingly, the amount of selenium in the present compositions is from 0 to maximum 0.1%, or at most 0.05%, optimally no more than 0.01%.

The inventive composition preferably includes a skin lightening compound, to obtain optimum skin lightening performance at an optimum cost. Illustrative substances are placental extract, lactic acid, resorcinols (4-substituted, 4,5-disubstituted, and 4,6 di-substituted, in particular 4-hexyl, 4-methyl, 4-butyl, 4-isopropyl, phenylethyl resorcinols), arbutin, kojic acid, ferulic acid, nicotinamide and derivatives, hydroquinone, resorcinol derivatives including disubstituted resorcinols and combinations thereof. In one embodiment, such skin lightening compound is a tyrosinase inhibitor, most preferably a compound selected from the group consisting of kojic acid, nicotinamide or derivatives, hydroquinone and other (non-4 substituted resorcinols). Also, dicarboxylic acids represented by the formula HOOC—(CxHy)-COOH where x=4 to 20 and y=6 to 40 such as azelaic acid, sebacic acid, oxalic acid, succinic acid, fumaric acid, octadecenedioic acid (e.g. Arlatone DC) or their salts or a mixture thereof, most preferably fumaric acid or salt thereof, especially di-sodium salt. It has been found that combination with 12HSA with fumaric acid or salts thereof are particularly preferred, especially for skin lightening formulations. Amounts of these agents may range from 0.1 to 10%, preferably from 0.5 to 2% by weight of the composition. It is preferred that the skin lightening coactive according to the invention is nicotinamide, and/or 4-alkyl resorcinol and/or 12-hydroxy stearic acid.

Another preferred ingredient of the inventive compositions is a retinoid. As used herein, "retinoid" includes all natural and/or synthetic analogs of Vitamin A or retinol-like compounds which possess the biological activity of Vitamin A in the skin as well as the geometric isomers and stereoisomers of these compounds. The retinoid is preferably retinol, retinol esters (e.g., $C_2$-$C_{22}$ alkyl esters of retinol, including retinyl palmitate, retinyl acetate, retinyl propionate), retinal, and/or retinoic acid (including all-trans retinoic acid and/or 13-cis-retinoic acid), more preferably retinoids other than retinoic acid. These compounds are well known in the art and are commercially available from a number of sources, e.g., Sigma Chemical Company (St. Louis, Mo.), and Boerhinger Mannheim (Indianapolis, Ind.). Other retinoids which are useful herein are described in U.S. Pat. No. 4,677,120, issued Jun. 30, 1987 to Parish et al.; U.S. Pat. No. 4,885,311, issued Dec. 5, 1989 to Parish et al.; U.S. Pat. No. 5,049,584, issued Sep. 17, 1991 to Purcell et al.; U.S. Pat. No. 5,124,356, issued Jun. 23, 1992 to Purcell et al.; and U.S. Pat. No. Reissue 34,075, issued Sep. 22, 1992 to Purcell et al. Other suitable retinoids are tocopheryl-retinoate [tocopherol ester of retinoic acid (trans- or cis-), adapalene {6-[3-(1-adamantyl)-4-methoxyphenyl]-2-naphthoic acid}, and tazarotene (ethyl 6-[2-(4,4-dimethylthiochroman-6-yl)-ethynyl]nicotinate). Preferred retinoids are retinol, retinyl palmitate, retinyl acetate, retinyl propionate, retinal and combinations thereof. The retinoid is preferably substantially pure, more preferably essentially pure. The compositions of this invention may contain a safe and effective amount of the retinoid, such that the resultant composition is safe and effective for regulating keratinous tissue condition, preferably for regulating visible and/or tactile discontinuities in skin, more preferably for regulating signs of skin aging, even more preferably for regulating visible and/or tactile discontinuities in skin texture associated with skin aging. The compositions preferably contain from 0.005% to 2%, or from 0.01% to 2%, retinoid. Retinol is preferably used in an amount of 0.01% to 0.15%; retinol esters are preferably used in an amount of from 0.01% to 2% (e.g., 1%); retinoic acids are preferably used in an amount of 0.01% to 0.25%; tocopheryl-retinoate, adapalene, and tazarotene are preferably used in an amount of from 0.01% to 2%.

A variety of herbal extracts may optionally be included in compositions of this invention. Illustrative are pomegranate, white birch (Betula alba), green tea, chamomile, licorice and extract combinations thereof. The extracts may either be water soluble or water-insoluble carried in a solvent which respectively is hydrophilic or hydrophobic. Water and ethanol are the preferred extract solvents.

Also included may be such materials as resveratrol, alpha-lipoic acid, ellagic acid, kinetin, retinoxytrimethylsilane (available from Clariant Corp. under the Silcare 1M-75 trademark), dehydroepiandrosterone (DHEA) and combinations thereof. Ceramides (including Ceramide 1, Ceramide 3, Ceramide 3B, Ceramide 6 and Ceramide 7) as well as pseudoceramides may also be utilized for many compositions of the present invention but may also be excluded. Amounts of these materials may range from 0.000001 to 10%, preferably from 0.0001 to 1%.

The personal care composition may further include about 0.1 wt % to about 8 wt % of a film forming polymer. Such film-forming polymers include, but are not limited to, polyalkyleneoxy terminated polyamides (e.g., INCI name: Polyamide-3, Polyamide-4), polyether polyamides (e.g., INCI name: Polyamide-6), mixed acid terminated polyamides (e.g., INCI name: Polyamide-7), and ester terminated poly (ester-amides) (e.g., INCI name: Polyamide-8). Such film forming polymers may be synthesized or are available commercially, such as under the Sylvaclear™ line of products by Arizona Chemical Company, LLC and the OleoCraft™ line of products by Croda International PLC. Film-forming polymers also include, but are not limited to, the INCI named Polyester-5 (e.g., Eastman AQ™ 38S Polymer), PPG-17/IPDI/DMPA Copolymer (e.g., Avalure™ UR 450 Polymer), Acrylates Copolymer (e.g., Avalure™ AC 120 Polymer), and polysaccharides such as Xilogel (tamarin gum), lotus bean gums, tara gum, beta glucan, pullulan, carboxymethyl cellulose, hydroxypropyl cellulose, sodium alginate, potato starch, carrageenan. The film forming polymer may include combinations of any two or more of the polymers recited above. The amount of film forming polymer in the personal care composition may be 0.1 wt % to 8 wt. %.

Preservatives can desirably be incorporated into the compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are iodopropynyl butyl carbamate, phenoxyethanol, caprylyl glycol, $C_{1-6}$ parabens (especially, methyl paraben and/or propyl paraben), imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from 0.01% to 2%. An especially preferred combination is octocrylene and caprylyl glycol, since caprylyl glycol has been disclosed to enhance UVA and UVB protection.

Anti-fungal agents suitable for inclusion in personal care compositions are well known to one of skill in the art. Examples include, but are not limited to, climbazole, ketoconazole, fluconazole, clotrimazole, miconazole, econazole, etaconazole, terbinafine, salts of any one or more of these (e.g., hydrochloride salts), zinc pyrithione, selenium disulfide, and combinations of any two or more thereof.

In some embodiments, the personal care compositions of the present invention include vitamins. Illustrative vitamins are Vitamin A (retinol), Vitamin B2, Vitamin B3 (niacinamide), Vitamin B6, Vitamin B12, Vitamin C, Vitamin D, Vitamin E, Vitamin K and Biotin. Derivatives of the vitamins may also be employed. For instance, Vitamin C derivatives include ascorbyl tetraisopalmitate, magnesium ascorbyl phosphate and ascorbyl glycoside. Derivatives of Vitamin E include tocopheryl acetate, tocopheryl palmitate and tocopheryl linoleate. DL-panthenol and derivatives may also be employed. In some embodiments, the Vitamin B6 derivative is Pyridoxine Palmitate. Flavonoids may also be useful, particularly glucosyl hesperidin, rutin, and soy isoflavones (including genistein, daidzein, equol, and their glucosyl derivatives) and mixtures thereof. Total amount of vitamins or flavonoids when present may range from 0.0001% to 10%, alternatively from 0.001% to 10%, alternatively from 0.01% to 10%, alternatively from 0.1% to 10%, alternatively from 1% to 10%, alternatively from 0.01% to 1%, alternatively from 0.1% to 0.5%.

In some embodiments, the personal care compositions of the present invention include an enzyme such as, for example oxidases, proteases, lipases and combinations thereof. In some embodiments, the personal care compositions of the present invention includes superoxide dismutase, commercially available as Biocell SOD from the Brooks Company, USA.

In some embodiments, the personal care compositions of the present invention include desquamation promoters. In some embodiments, the personal care compositions of the present invention include desquamation promoters at a concentration from 0.01% to 15%, alternatively from 0.05% to 15% alternatively from 0.1% to 15%, alternatively from 0.5% to 15%.

Illustrative desquamation promoters include monocarboxylic acids. Monocarboxylic acids may be substituted or unsubstituted with a carbon chain length of up to 16. In some embodiments, the carboxylic acids are the alpha-hydroxycarboxylic acids, beta-hydroxycarboxylic or polyhydroxycarboxylic acids. The term "acid" is meant to include not only the free acid but also salts and $C_1$-$C_{30}$ alkyl or aryl esters thereof and lactones generated from removal of water to form cyclic or linear lactone structures. Representative acids include glycolic, lactic, malic and tartaric acids. In some embodiments, the salt is ammonium lactate. In some embodiments, the beta-hydroxycarboxylic acid is salicylic acid. In some embodiments, the phenolic acids include ferulic acid, salicylic acid, kojic acid and their salts.

In some embodiments, the at least one additional component may be present from 0.000001% to 10%, alternatively from 0.00001% to 10%, alternatively from 0.0001% to 10%, alternatively from 0.001% to 10%, alternatively from 0.01% to 10%, alternatively from 0.1% to 10%, alternatively from 0.0001% to 1% by weight of the composition. Colorants, opacifiers or abrasives may also be included in compositions of the present invention. The colorants, opacifiers or abrasives may be included at a concentration from 0.05% to 5%, alternatively between 0.1% and 3% by weight of the composition.

In some embodiments, the personal care product of the present invention may also include a peptide, such as, for example, the commercially available pentapeptide derivative-Matrixyl™, which is commercially available from Sederma, France. In another example, in some embodiments, the personal care product of the present invention may also include Carnosine.

The compositions of the present invention can comprise a wide range of other optional components. The CTFA Cosmetic Ingredient Handbook, Second Edition, 1992, which is incorporated by reference herein in its entirety, describes a wide variety of non-limiting cosmetic and pharmaceutical ingredients commonly used in the topical cosmetic skin careindustry, which are suitable for use in the compositions of the present invention. Examples include: antioxidants, binders, biological additives, buffering agents, colorants, thickeners, polymers, astringents, fragrance, humectants, opacifying agents, conditioners, exfoliating agents, pH adjusters, preservatives, natural extracts, essential oils, skin sensates, skin soothing agents, and skin healing agents.

In one embodiment, the composition of the invention is a leave-on non-solid composition in the form of a personal care topical emulsion, lotion, gel, cream, or vanishing cream comprising glutathione precursor which comprises cystine, glutamate (especially pyroglutamic acid or salt thereof, e.g. sodium pyroglutamate) and nicotinamide, at pH of 3.5 to 8.5.

In one embodiment, the composition of the invention is a leave-on non-solid composition in the form of a personal care topical emulsion, lotion, gel, cream, or vanishing cream comprising glutathione precursor which comprises cystine, glycine, and nicotinamide, at pH of 3.5 to 8.5, especially at pH of 5 to 8.

In one embodiment, the composition of the invention is a leave-on non-solid composition in the form of a personal care topical emulsion, lotion, gel, cream, or vanishing cream comprising glutathione precursor which comprises cystine, glutamate (especially pyroglutamic acid or salt thereof, e.g. sodium pyroglutamate), glycine, and nicotinamide at pH of 3.5 to 8.5, especially at pH of 5 to 8.

In one embodiment, the composition of the invention is a leave-on non-solid composition in the form of a personal care topical emulsion, lotion, gel, cream, or vanishing cream comprising glutathione precursor which comprises cystine, glutamate (especially pyroglutamic acid or salt thereof, e.g. sodium pyroglutamate) and one or more of 4-hexylresorcinol, 4-ethylresorcinol, 4-isopropylresorcinol, 4-butylresorcinol, and 4-(1-phenylethyl)resorcinol, at pH of 3.5 to 8.5.

In one embodiment, the composition of the invention is a leave-on non-solid composition in the form of a personal care topical emulsion, lotion, gel, cream, or vanishing cream comprising glutathione precursor which comprises cystine, glutamate (especially pyroglutamic acid or salt thereof, e.g. sodium pyroglutamate), glycine, and 4-hexylresorcinol at pH of 3.5 to 8.5, especially at pH of 5 to 8.

In one embodiment, the composition of the invention is a leave-on non-solid composition in the form of a personal care topical emulsion, lotion, gel, cream, or vanishing cream comprising glutathione precursor which comprises cystine, glutamate (especially pyroglutamic acid or salt thereof, e.g. sodium pyroglutamate), glycine, and 4-butylresorcinol at pH of 3.5 to 8.5, especially at pH of 5 to 8.

In one embodiment, the composition of the invention is a leave-on non-solid composition in the form of a personal care topical emulsion, lotion, gel, cream, or vanishing cream comprising glutathione precursor which comprises cystine, glutamate (especially pyroglutamic acid or salt thereof, e.g. sodium pyroglutamate), glycine and 4-(1-phenylethyl)resorcinol at pH of 3.5 to 8.5, especially at pH of 5 to 8.

In one embodiment, the composition of the invention is a leave-on non-solid composition in the form of a personal care topical emulsion, lotion, gel, cream, or vanishing cream comprising glutathione precursor which comprises cystine, glutamate (especially pyroglutamic acid or salt thereof, e.g. sodium pyroglutamate), glycine, and 2-cyclopentyl-5-pentylresorcinol at pH of 3.5 to 8.5, especially at pH of 5 to 8.

In one embodiment, the composition of the invention is a leave-on non-solid composition in the form of a personal care topical emulsion, lotion, gel, cream, or vanishing cream comprising glutathione precursor which comprises cystine, glutamate (especially pyroglutamic acid or salt thereof, e.g. sodium pyroglutamate), glycine, and 5-pentyl-2-isopropylresorcinol at pH of 3.5 to 8.5, especially at pH of 5 to 8.

In one embodiment, the composition of the invention is a leave-on non-solid composition in the form of a personal care topical emulsion, lotion, gel, cream, or vanishing cream comprising glutathione precursor which comprises cystine, glutamate (especially pyroglutamic acid or salt thereof, e.g. sodium pyroglutamate), glycine and 5-ethyl-2-cyclopentylresorcinol at pH of 3.5 to 8.5, especially at pH of 5 to 8.

Form of the Composition

The water-in-oil compositions of the invention may be used as is. Alternatively, the water-in-oil emulsions of the present invention may be a component of final product which is water-in-oil or oil-in-water or multiple emulsions. The compositions of the invention are preferably leave-on compositions. The compositions of the present invention are preferably leave-on compositions to be applied to remain on the skin. These leave-on compositions are to be distinguished from compositions which are applied to the skin and subsequently removed either by washing, rinsing, wiping, or the like either after or during the application of the product. Surfactants typically used for rinse-off compositions have physico-chemical properties giving them the ability to generate foam/lather in-use with ease of rinse; they can consist of mixtures of anionic, cationic, amphoteric, and nonionic. Surfactants used in leave-on compositions on the other hand are not required to have such properties. Rather, as leave-on compositions are not intended to be rinsed-off they need to be non-irritating and therefore it is necessary to minimize the total level of surfactant and the total level of anionic surfactant in leave-on compositions. The total level of surfactant in the inventive compositions is preferably from 1% no more than 15%, more preferably below 10%, most preferably at most 9%, optimally at most 6%.

In some embodiments, anionic surfactants are present in the leave-on skin care composition in an amount of 0.01% to at most 5% by weight of the composition, alternatively from 0.01% to 4% by weight of the composition, alternatively from 0.01% to 3% by weight of the composition, alternatively from 0.01% to 2% by weight of the composition, alternatively substantially absent (less than 1%, or less than 0.1%, or less than 0.01%). In some embodiments, the total level of surfactant in the skin care compositions is no more than 15%, alternatively below 10%, alternatively at most 9%.

In some embodiments, the surfactant is selected from the group consisting of anionic, nonionic, cationic and amphoteric actives.

In some embodiments, nonionic surfactants are those with a $C_{10}$-$C_{20}$ fatty alcohol or acid hydrophobe condensed with from 2 to 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di-$C_8$-$C_{20}$ fatty acids; and polyoxyethylene sorbitan as well as combinations thereof. In some embodiments, the non-ionic surfactant is selected from the group consisting of alkyl polyglycosides, saccharide fatty amides (e.g. methyl gluconamides) and trialkylamine oxides.

Amphoteric surfactants suitable in skin care compositions according to some embodiments of the present invention include cocoamidopropyl betaine, $C_{12}$-$C_{20}$ trialkyl betaines, cocoamidopropyl hydroxysultaine, sodium lauroamphoacetate, and sodium laurodiamphoacetate.

Anionic surfactants suitable in skin care compositions according to some embodiments of the present invention include soap, alkyl ether sulfates and sulfonates, alkyl sulfates and sulfonates, alkylbenzene sulfonates, alkyl and dialkyl sulfosuccinates, $C_8$-$C_{20}$ acyl isethionates, $C_8$-$C_{20}$ alkyl ether phosphates, $C_8$-$C_{20}$ sarcosinates, $C_8$-$C_{20}$ acyl lactylates, sulfoacetates and combinations thereof.

The most preferred format are vanishing cream base and creams or lotions based on an water-in-oil emulsion. Vanishing cream base is one which comprises 5 to 40% fatty acid and 0.1 to 20% soap. In such creams, the fatty acid is preferably substantially a mixture of stearic acid and palmitic acid and the soap is preferably the potassium salt of the fatty acid mixture, although other counterions and mixtures thereof can be used. The fatty acid in vanishing cream base is often prepared using hystric acid which is substantially (generally about 90 to 95%) a mixture of stearic acid and palmitic acid. A typical hystric acid comprises about 52-55% palmitic acid and 45-48% stearic acid of the total palmitic-stearic mixture. Thus, inclusion of hystric acid and its soap to prepare the vanishing cream base is within the scope of the present invention. It is particularly preferred that the composition comprises higher than 7%, preferably higher than 10%, more preferably higher than 12% fatty acid. A typical vanishing cream base is structured by a crystalline network and is sensitive to the addition of various ingredients.

In some embodiments the personal care composition is formulated as a shampoo. In some embodiments, the personal care compositions of the present invention are formulated as a deodorant. In some embodiments, the personal care compositions of the present invention are formulated as an antiperspirant, e.g. according to the formulations described in U.S. Pat. No. 7,282,471.

In some embodiments, the personal care compositions of the present invention are formulated as a single use personal care towelette product as a single use personal care towelette product according to the formulations described in U.S. Pat. No. 7,282,471.

Method of Using the Skin Care Compositions

In some embodiments, the skin care composition is topically applied to human skin. In some embodiments, the skin care composition provides at least one benefit, selected from the group consisting of: skin conditioning, skin smoothening, reduction of wrinkled or aged skin, reduction of inflammation of the skin, reduction of dryness, reduction of age spots, an reduction of sun burn, and lightening of the skin.

In some embodiments, a small quantity of the skin care composition, for example from 1 to 5 ml, is applied to exposed area of the skin, from a suitable container or applicator and, if necessary, it is then spread over and/or rubbed into the skin using the hand or fingers or a suitable device. Alternatively, a small quantity of the skin care composition, for example from 1 to 5 ml, is applied to exposed area of the skin, from a suitable container or applicator and then covered by mask, non-woven, or film-former.

Reference is now made to the following examples, which together with the above descriptions illustrate some embodiments of the invention in non-limiting examples.

EXAMPLES

Emulsions were prepared as follows:

Step 1 was to make two aqueous solutions. Solution 1 was a high pH cystine solution that solubilized desired level of cystine. Solution 2 was an acidic solution used to neutralize solution 1 to the target final pH of the aqueous phase in the emulsion. In step 2, a water-in-oil pre-emulsion was prepared using low energy shear devices by loading aqueous solution 1 to the oil phase that contained the emulsifier. When solution 1 was completely loaded, the acidic solution 2 was added. During step 3, the pre-emulsion is homogenized or sonolated. Emulsions that were obtained are summarized in Table 1 below. There was no phase separation and no precipitation observed during and after the emulsions were made.

TABLE 1

| | Sample 1 wt % | Sample 2 wt % | Sample 3 wt % |
|---|---|---|---|
| water, pH 10-10.5 (solution 1) | 29.7 | 40 | 46 |
| NaCl | 0.4 | 0.3 | 0.3 |

TABLE 1-continued

|  | Sample 1 wt % | Sample 2 wt % | Sample 3 wt % |
| --- | --- | --- | --- |
| EDTA | 0.4 | 0.3 | 0.3 |
| Cystine | 0.4 | 0.3 | 0.3 |
| Water/Citric acid (Solution 2) | 20 | 16.4 | 19 |
| Aqueous phase | 50.9 | 57.3 | 65.9 |
| Oil Phase | 49.1 | 42.7 | 34.1 |
| caprylic/capric triglyceride (CCT) | 44.1 | 36.7 | 28.4 |
| ES5300 | 5 | 6 | 5.7 |
| Presence of Drops greater than 20 microns | No | No | Yes |
| Cystine crystallization | No | No | Yes |

Cystine Crystalization Analysis by SEM and Microscope Images

The L-Cystine crystallization behavior was studied by using cryo SEM, as follows:

A 3 microliter of sample was loaded on an aluminum pin and plunged frozen in liquid propane cooled by liquid nitrogen. Sample was cryotransferred into the cryo chamber of microtome (Leica Ultracut UCT EM FC7) and cryo-planned at temperature (minus 145°) C. The sample was cryo transferred into Gatan Alto 2500 cryostage and etched at −90° C. and coated with Au—Pd. Then the sample was inserted into Hitachi 4700 SEM and examined at −135° C. and 5 KV, WD 12 mm.

SEM image for samples 1 and 2 versus sample 3 demonstrated the presence of some drops larger than 20 microns in sample 3.

In Samples 1 and 2, there were no emulsion droplets greater than 20 microns and in these samples no cystine crystals were observed. On the other hand, sample 3 contained some emulsion drops that were greater than 20 microns with cystine crystals present only in these larger drops.

The results in Example 1 demonstrate that cystine crystal formation is dependent on the size of the droplets. In Samples 1 and 2, cystine was present in an amount of about 0.3 wt % a value approximately 30 times higher than its natural solubility limit of 0.01 wt % at room temperature and neutral pH.

Example 2

Chemical Stability

Cystine chemical stability was evaluated at room temperature and after storage at 45° C. for 30 days. Samples 1, 2 and 3 were prepared by the inventive process. Sample 4 was a duplicate of sample 2 except here the sample was prepared solely by dissolving the cystine at high pH without subsequent neutralization with acidic solution

TABLE 2

| Sample | % Cystine Spec | % Cystine Actual Initial | % Cystine 20 days at RT* | % Cystine 30 days at RT | % Cystine 12 days at 45° C. | % Cystine 30 days at at 45° C. |
| --- | --- | --- | --- | --- | --- | --- |
| Sample 1, pH 5.5 | 0.40 | 0.38 | 0.40 | 0.35 | 0.37 | 0.37 |
| Sample 2, pH 5.5 | 0.33 | 0.31 | 0.32 | 0.29 | 0.28 | 0.31 |
| Sample 3, pH 5.5 | 0.26 | 0.24 | Phase separated |  | 0.00 |  |
| Sample 4 with high pH solution only, pH 10.5 | 0.33 | 0.31 | 0.31 | 0.27 | 0.30 ± 0.03 | 0.14 |

*Room temperature

The results in table 2 illustrate that cystine levels in water-in-oil emulsions prepared by the inventive process, i.e. samples 1 and 2, retained greater than 90% cystine. Sample 3 outside the scope of the invention, phase separated and analysis could not be done; the phase separation also resulted in cystine crystallization. Sample 4 which was not neutralized with acid had less than 50% cystine retained.

Example 3

Personal care formulations according to the present invention are illustrated in the Tables below. All numbers in the Tables represent weight % in the composition.

TABLE I

| Oil-in-water formulations, lotions, and creams | | | | | |
| --- | --- | --- | --- | --- | --- |
|  | OW-1 | OW-2 | OW-3 | OW-4 | OW-5 |
| Water | To 100 | To 100 | To 100 | To 100 | To 100 |
| Glycerine | 0-40 | 1-40 | 1-5 | 1-10 | 1-40 |
| Propylene glycol | 0-5 |  | 0-5 |  |  |
| Butylene glycol | 0-5 |  | 0-5 | 0-5 |  |
| Carbomer | 0-2 | 0.03-1 |  |  |  |

TABLE I-continued

Oil-in-water formulations, lotions, and creams

| | OW-1 | OW-2 | OW-3 | OW-4 | OW-5 |
|---|---|---|---|---|---|
| Ammonium Acryloyl dimethyl taurate/VP copolymer | 0-1 | | 0.03-1 | | 0.01-1 |
| Styrene/Acrylates copolymer | 0-1 | | 0.01-1 | | |
| Xanthan Gum | 0-1 | | | | 0.01-1 |
| EDTA | 0.01-0.01 | 0.01-0.01 | 0.01-1 | 0.01-1 | 0.01-1 |
| Preservative | 0.02-2 | 0.02-2 | 0.02-2 | 0.02-2 | 0.02-2 |
| Titanium oxide | 0-10 | 0.01-10 | 0.01-10 | 0.01-10 | 0.01-10 |
| Colorant/Pigment | 0-5 | 0-5 | 0-5 | 0-5 | 0-5 |
| Triethanol amine/Sodium Hydroxide/potassium Hydroxide | 0-3 | 0.01-3 | 0.01-3 | 0.01-3 | 0.01-3 |
| Stearic acid | 0-5 | 0.01-5 | 0.01-5 | 0.01-5 | 0.01-5 |
| Isopropyl Myristate | 0-10 | 0.01-10 | | | |
| Capric/Caprylic Triglyceride | 0-10 | 0.01-10 | | | |
| C12-C15 alkyl benzoate | 0-10 | | | | 0.01-10 |
| Mineral oil | 0-10 | | | 0.01-10 | |
| Glyceryl stearate | 0-5 | 0.01-5 | | | |
| Steareth-2 | 0-5 | | 0.01-5 | | 0.01-5 |
| Steareth-21 | 0-5 | | 0.01-5 | | |
| Peg100 Stearate | 0-5 | | | 0.01-2 | 0.01-5 |
| Potassium Cetyl Phosphate | 0-5 | | | 0.01-2 | |
| Tween20 | 0-5 | | | | 0.01-5 |
| Cetyl alcohol | 0-4 | 0.01-4 | | 0.01-4 | |
| Dicaprylyl carbonate | 0-5 | | 0.01-5 | | |
| Ethyl hexyl methoxycinnamate | 0-6 | 0.01-6 | | | |
| Butyl Methoxydibenzoylmethane | 0-3 | 0.01-3 | | 0.01-3 | 0.01-3 |
| Ensulizole | 0-4 | | | | 0.01-4 |
| Octinoxate | 0-7.5 | | | | |
| Octisalate | 0-5 | | | 0.01-5 | 0.01-5 |
| Octocrylene | 0-10 | | | 0.01-10 | 0.01-10 |
| Homosalate | 0-10 | | | 0.01-10 | |
| Dimethicone | 0-10 | 0.01-10 | 0.01-10 | | |
| Cyclomethicone | 0-15 | | 0.01-15 | | |
| Niacinamide | 0-5 | 0-5 | 0-5 | 0-5 | 0-5 |
| Fragrance | 0-2 | 0-2 | 0-2 | 0-2 | 0-2 |
| Glutamine/Sodium PCA | 0.01-10 | 0.01-10 | 0.01-10 | 0.01-10 | 0.01-10 |
| Glycine | 0.01-10 | 0.01-10 | 0.01-10 | 0.01-10 | 0.01-10 |
| Cystine | 0.001-2 | 0.001-2 | 0.001-2 | 0.001-2 | 0.001-2 |
| 2-Cyclopentyl-5-pentylresorcinol | 0.001-3 | | | | 0.001-3 |
| 5-pentyl-2-isopropylresorcinol | | 0.001-3 | | | |
| 5-pentyl-2-cyclopentylresorcinol | | | 0.001-3 | | 0.001-3 |

TABLE II

Water-in-oil topical lotions or creams

| | WO-1 | WO-2 | WO-3 | WO-4 |
|---|---|---|---|---|
| Water | To 100 | To 100 | To 100 | To 100 |
| Glycerine | 0-70 | 1-70 | 1-70 | |
| Propylene glycol | 0-5 | | | 0.01-5 |
| Butylene glycol | 0-5 | | 0.01-5 | 0.01-5 |
| Disteardimonium Hectorite | 0.01-1 | 0.01-1 | | |
| EDTA | 0.01-.01 | 0.01-1 | 0.01-1 | 0.01-1 |
| Preservative | 0.02-2 | 0.02-2 | 0.02-2 | 0.02-2 |
| TiO2 | 0-10 | 0.01-10 | 0.01-10 | 0.01-10 |
| Colorant/pigment | 0-5 | 0-5 | 0-5 | 0-5 |
| TEA/Sodium Hydroxide/potassium Hydroxide | 0-3 | 0.01-3 | 0.01-3 | 0.01-3 |
| Stearic acid | 0-5 | 0.01-5 | | |
| Isopropyl Myristate | 0-10 | | | |
| Capric/Caprylic Triglyceride | 0-10 | | 0.01-10 | |
| C12-C15 alkyl benzoate | 0-10 | | | 0.01-10 |
| Mineral oil | 0-10 | | | |
| Glyceryl stearate | 0-5 | | | |
| Dimethicone copolyol | 0-5 | 0.01-5 | 0.01-5 | |
| Cetyl PEG/PPG-10/1 Dimethicone | 0-5 | | | 0.01-5 |
| Steareth-2 | 0-2 | | | |
| Sucrose Distearate | 0-2 | 0.01-2 | | |
| Cetyl alcohol | 0-2 | 0.01-2 | 0.01-2 | |
| Ethyl hexyl methoxycinnamate | 0-6 | 0.01-6 | | |
| Butyl Methoxydibenzoylmethane | 0-3 | 0.01-3 | 0.01-3 | 0.01-3 |

TABLE II-continued

| Water-in-oil topical lotions or creams | | | | |
|---|---|---|---|---|
| | WO-1 | WO-2 | WO-3 | WO-4 |
| Ensulizole | 0-4 | | 0.01-4 | |
| Octinoxate | 0-7.5 | | | |
| Octisalate | 0-5 | | 0.01-5 | 0.01-5 |
| Octocrylene | 0-10 | | 0.01-10 | 0.01-10 |
| Homosalate | 0-10 | | | 0.01-10 |
| Dimethicone | 0-10 | | 0.01-10 | 0.01-10 |
| Cyclomethicone | 0-40 | 0.01-40 | | 0.01-10 |
| Caprylyl methicone | 0-10 | 0.01-10 | | 0.01-10 |
| Dimethicone crosspolymer | 0-90 | 0.01-90 | 0.01-90 | |
| C30-C45 alkyl cetearyl dimethicone crosspolymer | | | | 0.01-90 |
| Glycolic acid | 0-10 | 0.01-10 | | |
| KCl | 0-5 | 0.01-5 | 0.01-5 | 0.01-5 |
| lacinamide | 0-5 | 0.01-5 | 0.01-5 | 0.01-5 |
| Fragrance | 0-2 | 0-2 | 0-2 | 0-2 |
| Glutamine/Sodium PCA | 0.01-10 | 0.01-10 | 0.01-10 | 0.01-10 |
| Glycine | 0.01-10 | 0.01-10 | 0.01-10 | 0.01-10 |
| Cystine | 0.001-2 | 0.001-2 | 0.001-2 | 0.001-2 |
| 4-hexylresorcinol | 0.001-3 | | | |
| 4-ethylresorcinol | | 0.001-3 | | |
| 4-butylresorcinol | | | 0.001-3 | |
| 4-(1-phenylethyl)resorcinol | | | | 0.001-3 |

TABLE III

| Vanishing Creams | | | | |
|---|---|---|---|---|
| | VC-1 | VC-2 | VC-3 | VC-4 |
| Water | To 100 | To 100 | To 100 | To 100 |
| Glycerine | 0-5 | 0.01-5 | 0.01-5 | |
| EDTA | 0.01-.01 | 0.01-.01 | 0.01-.01 | 0.01-.01 |
| Preservative | 0.02-2 | 0.02-2 | 0.02-2 | 0.02-2 |
| TiO2 | 0.01-10 | 0.01-10 | 0.01-10 | 0.01-10 |
| Colorant/pigment | 0-5 | 0.01-5 | 0.01-5 | |
| TEA/Sodium Hydroxide/potassium Hydroxide | 0-3 | 0.01-3 | 0.01-3 | 0.01-3 |
| Stearic acid | 0-30 | 0.01-30 | 0.01-30 | 0.01-30 |
| Isopropyl Myristate | 0-5 | 0.01-10 | 0.01-10 | |
| C12-C15 alkyl benzoate | 0-5 | | | 0.01-10 |
| Brij 35 | 0-5 | 0.01-5 | | |
| Tween40 | 0-5 | | | 0.01-5 |
| Cetyl alcohol | 0-2 | 0.01-2 | 0.01-2 | |
| Ethyl hexyl methoxycinnamate | 0-6 | 0.01-6 | 0.01-6 | |
| Butyl Methoxydibenzoylmethane | 0-3 | 0.01-3 | 0.01-3 | 0.01-3 |
| Ensulizole | 0-4 | | | 0.01-4 |
| Octisalate | 0-5 | | | 0.01-5 |
| Octocrylene | 0-10 | | 0.01-10 | 0.01-10 |
| Dimethicone | 0-5 | 0.01-5 | | |
| Cyclomethicone | 0-5 | | | 0.01-5 |
| Dimethicone crosspolymer | 0-4 | | | 0.01-4 |
| Hydroxystearic acid | 0-5 | 0.01-5 | 0.01-5 | 0.01-5 |
| Fragrance | 0-2 | 0-2 | 0-2 | 0-2 |
| Glutamine/Sodium PCA | 0.01-10 | 0.01-10 | 0.01-10 | 0.01-10 |
| Glycine | 0.01-10 | 0.01-10 | 0.01-10 | 0.01-10 |
| Cystine | 0.001-2 | 0.001-2 | 0.001-2 | 0.001-2 |
| Nicotinamide | 0.01-5 | 0.01-5 | 0.01-5 | 0.01-5 |

The invention claimed is:

1. A process of making a topical water-in-oil personal care emulsion composition, the process comprising the steps of
   a. mixing from about 0.5 to about 10% of cystine in basic aqueous solution at pH of from 9 to 14, to obtain an aqueous solution of cystine;
   b. mixing the aqueous solution of cystine with a cosmetically acceptable oil and with from 1 to 15% of an emulsifier with HLB from 1 to 12, to obtain a water-in-oil pre-emulsion;
   c. mixing the pre-emulsion with an aqueous acidic solution at pH of from 1 to 4.5; and
   d. reducing the pH of the pre-emulsion to the pH range of from 3.5 to 8.5 and reducing the droplet size of the aqueous phase in the pre-emulsion such that from 90% to 100% of the droplets have a diameter in the range of from 100 nm to 20 microns, wherein the emulsion comprises from 10 to 70% of aqueous phase, with the weight ratio of the basic aqueous solution to the acidic aqueous solution is in the range of from 4:1 to 1:1.

2. The process of claim 1 wherein the acidic aqueous solution comprises an acid selected from the group consisting of mineral acids, fatty acids, hydroxycarboxylic acid, di-carboxylic acid, polycarboxylic acid, and mixtures thereof.

3. The process according to claim 1 wherein steps c. and d. are carried out simultaneously.

4. The process according to claim 1 wherein the viscosity of the emulsion is in the range of from 1 Pas to 500 Pas as measured at 20 degrees Celsius.

5. The process according to claim 1 wherein step d. comprises subjecting the pre-emulsion to high shear.

* * * * *